United States Patent [19]
May

[11] Patent Number: 5,276,194
[45] Date of Patent: Jan. 4, 1994

[54] POLYFLUOROALKYLATION OF AROMATIC COMPOUNDS

[75] Inventor: Donald D. May, Chadds Ford, Pa.

[73] Assignee: E. I. Du Pont de Nemours and Company, Wilmington, Del.

[21] Appl. No.: 59,184

[22] Filed: May 7, 1993

Related U.S. Application Data

[63] Continuation-in-part of Ser. No. 843,749, Feb. 28, 1992, abandoned.

[51] Int. Cl.$^5$ .................... C07C 209/00; C07C 43/02; C07C 25/13
[52] U.S. Cl. .................................. 564/409; 568/628; 570/144
[58] Field of Search ..................... 570/144; 568/628; 564/409

[56] References Cited

FOREIGN PATENT DOCUMENTS 3247728  7/1984  Fed. Rep. of Germany ...... 570/144

*Primary Examiner*—Alan Siegel

[57] ABSTRACT

A process is provided for the catalytic perfluoroalkylation of aromatic compounds, wherein a perfluoroalkyl iodide or mixture of iodides is reacted with an aromatic compound in the presence of an aqueous base, such as an alkali metal hydroxide or carbonate. The use of an aqueous strong base increases the rate of reaction. Further improvements in rate and yield are secured by employing, as the catalyst, a noble metal supported on porous silica microspheres.

10 Claims, No Drawings

POLYFLUOROALKYLATION OF AROMATIC COMPOUNDS

This is a continuation-in-part of application Ser. No. 07/843,749 filed Feb. 28, 1992, now abandoned.

FIELD OF THE INVENTION

This invention relates to a process for fluoroalkylation of aromatic compounds. It relates also to novel products produced thereby. More especially this invention relates to the preparation of polyfluoroalkyl aromatic compounds by the metal-catalyzed reaction of a perfluoroalkyl iodide with an aromatic compound.

BACKGROUND OF THE INVENTION

Catalytic perfluoroalkylation of aromatic compounds is known in the art. The process, as taught in the art, provides a method whereby an unfunctionalized aromatic group is substituted with a perfluoroalkyl group with the concurrent production of hydrogen iodide. A process for the catalytic addition of perfluoroalkyl iodide to benzene using a ruthenium catalyst on carbon and employing solid potassium carbonate as a hydrogen iodide acceptor is disclosed in European Patent Application No. 0 114 359 of Werner. Good yields of the perfluoroalkyl benzene are reported but only when large amounts of catalyst are used.

SUMMARY OF THE INVENTION

The present invention is an improvement in a process for the catalyzed fluoroalkylation of aromatic compounds, the improvement comprising conducting the fluoroalkylation reaction with a supported metal catalyst, in the presence of an aqueous base. The improvement is, in effect, a method for increasing the rate of reaction during the catalyzed fluoroalkylation of aromatic compounds. The preferred base is aqueous potassium hydroxide or aqueous potassium carbonate and the preferred catalyst is palladium and/or platinum on silica prepared as described in commonly assigned, copending application U.S. Ser. No. 07/587,879 filed Sep. 25, 1990, the disclosure of which is specifically incorporated herein by reference. Conducting the fluoroalkylation reaction in the presence of aqueous base unexpectedly increases the rate of reaction by a factor of up to about 20:1 in comparison to the rate of reaction achieved by Werner in the aforesaid European Patent Application. Furthermore, conducting the fluoroalkylation with catalysts of the type described in the above copending U.S. application may increase the rate of reaction by a factor of up to about 9:1 when compared to the rate achieved in accordance with the present invention when using a Pd on Catalyst. By employing the two features in combination the rate of fluoroalkylation may be about increased by a factor of about 36 over the prior art processes.

DETAILED DESCRIPTION OF THE INVENTION

The process of the invention can be conveniently expressed by the following reaction:

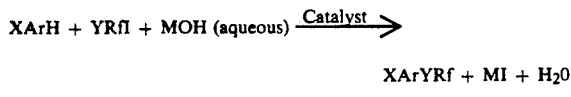

The Aromatic Compound (XArH)

The aromatic compound should have at least one unsubstituted position (represented by "H") and may contain one or more substituents (represented by "X"). A wide range of aromatic compounds are usable in the invention. In general, any carbocyclic or heterocyclic compound, including polymers, which is susceptible to electrophilic attack is suitable for use in the process of this invention. Such compounds will generally be those which are defined by the Huckel rule. The term "aromatic compound" as used in this application should be understood to include all such compounds. Unsubstituted aromatic compounds such as benzene, naphthlene and anthracene are suitable for use in the invention. Alkyl, halo (especially chloro and bromo), cyano, sulfonate, hydroxyl, nitro, alkyloxy and amino substitution do not prevent reaction. The nature of the substituent may affect the rate of reaction; for example toluene reacts faster than benzene but nitrobenzene is slower than benzene. In some cases, however, substituents may themselves undergo reaction. For example benzonitrile reacts cleanly in accordance with the invention to give a mixture of perfluoroalkylbenzoic acids rather than the corresponding nitrile. Multiply-substituted aromatic compounds also undergo reaction. Heteroaromatic compounds such as pyridine, thiophene and furan also undergo reaction. These heteroaromatic materials may also bear substitution.

Polymers such as polystyrene, polystyrene sulfonate and styrene/maleic acid copolymers also undergo reaction. The introduction of the perfluoroalkyl group tends to impart oil and water repellency properties to polymers. In the case of styrene/maleic acid or anhydride copolymers, the perfluoroalkylated derivatives are new compositions of matter which are useful as dry soil agents for treatment of fabrics and textiles to impart oil and water repellency. In the preferred styrene/maleic acid copolymers there are about 7 to 8 repeating units and 3 to 4 styrene groups. The styrene groups in the above polymers and copolymers are generally perfluoroalkylated in the para positions.

In addition, the perfluoralkylated aromatic compounds of the present invention are useful as intermediates in the preparation of pharmaceuticals, dyestuffs and agricultural chemicals.

The Base (MOH)

Useful bases are those in which the resulting iodide (MI) is stable under the conditions of the reaction. The base is preferably inorganic more preferably a hydroxide, carbonate or bicarbonate of a Group IA or Group IIA metal, e.g. potassium, sodium or lithium hydroxide, carbonate or bicarbonate. The most preferred bases are strong inorganic bases, e.g. alkali metal hydroxides, carbonates and bicarbonates such as potassium hydroxide and potassium carbonate. The base may be charged to the reaction in the form of an aqueous solution. In the alternative, the base may be charged to the reactor as a solid, and the water used to dissolve it (i.e. "solvent water") added to the reactor separately. The amount of solvent water must be sufficient to dissolve all of the base under the conditions employed in the reaction, e.g., temperature and pressure. Generally the concentration of base in solvent water will be 6 weight percent or greater. Preferably a concentrated aqueous solution of the base is employed, e.g. at least about 30% by weight, typically about 50% by weight. It is also preferable to use at least one mole of base is used per mole of perfluoroalkyl iodide. No significant disadvantage is seen by employing several moles of base per mole of iodide.

The Fluoroalkyl Iodide (YRfI)

Either a single fluoroalkyl iodide or a mixture of iodides may be used. Typically the Rf radical is a straight chain fluoroalkyl residue containing 1 to 20 carbon atoms or a mixture of such iodides may be employed. Preferably, the Rf radical contains about 4 to 16 carbon atoms. As indicated in the above reaction equation the iodide may include a substituent Y which may be F, Cl, Br or H, although F is preferred. It has incidentally been found that perfluoroalkyl bromide gives negligible reaction at 200° C. and 18 hours. Preferably an excess of aromatic compound is employed. This reduces multiple perfluoroalkylation side reactions. Typically the mole ratio of aromatic compound to perfluoralky iodide is in the range of 2:1 to 4:1. In a more preferred embodiment, one uses a mixture of perfluoroalkyl iodides having the formula:

$$F(CF_2)_a$$

wherein a is predominantly 6, 8 and 10. In a typical mixture, the compounds will have the following approximate composition in relation to their $F(CF_2)_a$ radicals:

0% to 3% wherein a=4,
27% to 37% wherein a=6,
28% to 32% wherein a=8,
14% to 20% wherein a=10,
8% to 13% wherein a=12,
3% to 6% wherein a=14,
0% to 2% wherein a=16,
0% to 1% wherein a=18, and
0% to 1% wherein a=20

Other fluorochemical reagents which can be used include a perfluoroalkyl iodide mixture (FNI) of the formula shown below wherein a is predominantly 8, 10 and 12. In a typical mixture of such fluoroalcohols, the compounds will have the following approximate composition in relation to their $F(CF_2)_a$ radicals:

0% to 3% wherein a=6,
45% to 52% wherein a=8,
26% to 32% wherein a=10,
10% to 14% wherein a=12,
2% to 5% wherein a=14,
0% to 2% wherein a=16,
0% to 1% wherein a=18, and
0% to 1% wherein a=20

Water

The precise amount of water appears not to be critical to the invention provided that during the reaction there is sufficient water to dissolve all of the base; However, since water is a product of the reaction, the initial concentration of the aqueous base is generally high. Typically the water and base are added in the form of concentrated, e.g. about 50%, aqueous solutions of the base. It is not necessary for the base to be dissolved in the water prior its introduction into the other reactants, the base may be added as solution in water or solid base may be added to the reactor and then combined with sufficient water in the reactor.

The Catalyst

A range of noble and transition metal catalysts can be employed. Examples include rhodium, palladium, platinum, ruthenium, cobalt, nickel and rhenium, preferably on an inert support such as carbon, alumina, titania, silica, barium carbonate, barium sulfate or calcium carbonate. The support preferably as a high surface area, e.g. about 100 m$^2$/gram or greater. Raney nickel, Raney copper or Raney cobalt composition catalysts are also usable. Ni on C and Co on C are also effective catalysts. The preferred catalysts are palladium and/or platinum on silica catalysts of the kind disclosed in the above-mentioned co-pending application U.S. Ser. No. 07/587 879, the disclosure of which is specifically incorporated herein. Typical amounts of catalyst are about 0.05 to about 0.5 weight percent based on perfluoroalkyl iodide. On a molar basis the catalyst metal is normally employed in an amount of from about $10^{-6}$ to 1 mole per mole of polyfluoroalkyl iodide, preferably from about $10^{-5}$ to $10^{-2}$ mole of catalyst metal per mole of perfluoroalkyl iodide.

These preferred catalysts can be made by either of two processes; designated herein as "Process #1" or "Process #2". Process #1 comprises the steps of:
(a) preparing an aqueous solution of a metal salt or metal salts of the catalytic metal, e.g. platinum and/or palladium;
(b) dissolving an ammonium citrate additive in said solution;
(c) adding an aqueous sol of colloidal silica particles, having a diameter in the range of 5 to 100 nanometres;
(d) spray-drying the mixture to form a powder consisting of microspherical silica particles, said particles comprising a conglomerate of the original silica particles with metal salts and ammonium citrate or urea distributed throughout;
(e) calcining to remove volatile components and to sinter the colloidal silica particles within the microspheres without fusing the microspheres into agglomerates; and
(f) heating in a hydrogen atmosphere.

Process #1 can be modified by adding a urea additive to step (c) thereby eliminating step (b).

Process #2 comprises the steps of:
(a) mixing an aqueous sol of colloidal silica particles, having a diameter in the range of 5 to 100 nm, with an effective amount of a soluble additive selected from ammonium citrate or urea;
(b) spray-drying the mixture to form a powder consisting of microspherical silica particles and ammonium citrate or urea, said particles comprising a conglomerate of the original colloidal silica particles and said additive;
(c) calcining the spray dried powder to remove volatile components and to sinter the colloidal silica particles within the microspheres without fusing the microspheres into agglomerates;
(d) adding one or more metal salts thus-formed silica microspheres which are then heated in a hydrogen atmosphere.

The product of Process #1 and Process #2 are attrition-resistant porous microspheres of silica having crystalites of the catalyst metal dispersed throughout the microspheres.

The reaction can be performed without organic solvent or using the aromatic compound XArH as solvent. In this case a two phase system will typically be obtained. An inert water soluble co-solvent such as tetrahydrofuran, dimethyl formamide, methanol or other alcohol can be employed. The preferred method is to use XArH as the solvent, since its use reduces polyperfluoroalkylation. Of course, where the aromatic compound is a solid a substantially inert organic solvent should be employed.

Typical reaction temperatures are in the range of about 150° C. to about 250° C. Reaction pressure is not critical although increased pressure increases reaction rate. Conveniently reaction may take place in a sealed 'bomb'. The pressure rises during heating typically to a pressure of the order of 35 bar at about 200° C.

The rate of reaction is further improved by use of a phase transfer agent since this facilitates the removal of the inorganic iodide product of the reaction. Any phase transfer agent which is not subject to decomposition under the reaction conditions of this invention (e.g. temperature) is suitable, e.g. alkoxyalkylamines. Efficient and continuous stirring of the reactants is also beneficial and the reaction is preferably carried out under conditions of continuous stirring or agitation.

The following examples serve to illustrate the invention. Unless otherwise stated all percentages are by weight. Catalytic perfluoroalkylations are run in a 125 ml pressure vessel fitted with a magnetic stirring bar and an internal thermocouple to measure temperature, a gauge to read pressure and a pressure relief device. Heating is provided by an external thermostatted oil bath. This apparatus is herein referred to as Reactor I.

EXAMPLE 1

The following reactants were charged into Reactor I:

|  | g |
| --- | --- |
| Benzene | 20 |
| Perfluorobutyl iodide (PFBI) | 36 |
| 50% aqueous potassium carbonate | 10 |

To the above mixture was added 0.5 grams of a catalyst consisting of 2% palladium and 0.1% platinum on a silica support (prepared in accordance with Process #1). The mixture was heated with stirring for 30 hours at 170° C. After reaction, the contents were discharged, washed with water, and the organic layer analyzed by Gas Chromatography (GC) employing an internal standard and experimentally determined response factors. There was no unreacted PFBI and there was a 93% yield of perfluorobutyl benzene and a 5 percent yield of mixed diperfluorobutyl benzene isomers.

COMPARATIVE EXAMPLE 1

The following reactants were charged into Reactor I:

|  | g |
| --- | --- |
| Benzene | 20 |
| PFBI | 36 |
| Anhydrous Potassium Carbonate | 5 |

To the above mixture was added 0.5 grams of the same catalyst as that used in Example 1. The contents were heated for 30 hours at 170° C. After reaction, the contents were worked-up and analyzed as before to give a 4% yield of perfluorobutyl benzene. This experiment shows, when compared with Example 1 that addition of water to the reaction system improves the yield by (93%/4) i.e., 23 times that obtained without the addition of water for the same duration of reaction.

The following two Examples are illustrative of the reaction employing ruthenium on carbon as catalyst.

EXAMPLE 2

Into a 1 liter Monel high pressure autoclave (herein referred to as Reactor II) fitted with a double pitched turbine agitator (540 rpm), an internal cooling coil wound the entire length of the vessel, and heated by an external electrical resistance heater were placed the following:

|  | g |
| --- | --- |
| Benzene | 234 |
| PFBI | 194 |
| 50% aqueous Potassium carbonate | 100 |
| Catalyst 5% Ru on carbon | 25 |

The contents were stirred and heated to 170° C. (internal temperature) for 30 hours. After reaction a phase cut was taken and the organic phase analyzed by Quantitative Gas Chromatography (QGC) employing an internal standard. Analysis showed there to be a 55 percent yield of perfluorobutyl benzene and a 1 percent yield of mixed diperfluorobutyl benzene isomers. The remainder of the perfluorobutyl iodide (43 percent) remained unreacted.

COMPARATIVE EXAMPLE 2

Reactor II was charged with the following ingredients:

|  | g |
| --- | --- |
| Benzene | 234 |
| PFBI | 194 |
| Anhydrous | 50 |
| Potassium carbonate |  |
| Catalyst 5% Ru on carbon | 25 |

The mixture was subjected to the same reaction conditions as Example 2. The ingredients were taken from the same bottle as used in Example 2. After reaction the contents were worked up as before and the organic phase contained a 10% yield of perfluorobutyl benzene. The remainder of the perfluorobutyl iodide (96%) was unreacted.

Example 2 and its comparative Example shows that addition of water to the reaction system improved the yield by (55%/10%), i.e., 5.5 times that obtained without the addition of water.

EXAMPLE 3

Reactor I was charged with the following reactants:

|  | g |
| --- | --- |
| Benzene | 20 |
| PFBI | 36 |
| 50% aqueous potassium carbonate | 15 |

To the above reactants was added 0.5 grams of a catalyst consisting of 2% Pd on silica microspheres, prepared as described in U.S. Ser. No. 07/587,879. The reactor was purged with nitrogen, and heated to 200° C. for 14 hours. After the specified reaction time, the contents are cooled, filtered to remove catalyst, and the phases were separated. The organic layer was then analyzed by QGC using an internal standard and known response factors. The yield of perfluorobutyl benzene (I) was 88% with 4% diperfluorobenzene isomers (III). The organic layer was placed into a distillation column and distilled at atmospheric pressure. A fraction boiling at 149°-151° C. was obtained which analyzed as 98% perfluorobutyl benzene (m/e=296, base peak=127) with the remaining 2% containing diperfluorobutyl benzene isomers. The total weight of the fraction was 24 g.

EXAMPLE 4

The reaction described in Example 3 was repeated except 60 g of mixed C4–C10 perfluoroalkyl iodides (telomer iodides) were added instead of perfluorobutyl iodide. The yield of perfluoroalkyl benzene was 85% based on starting perfluoroalkyl iodides.

EXAMPLE 5

The reaction described in Example 1 was repeated using 0.1 mole of PFBI and 0.2 mole of naphthalene at 200° C. for 14 hours. Conversion of the PFBI was quantitative and the fluoroalkyl substitution on the naphthalene was 53% alpha, 17% beta and 30% distribution.

EXAMPLE 6

Example 5 was repeated using an equivalent amount of anthracene in place of naphthalene. Ten percent of the PFBI was converted to perfluorobutylanthracene.

EXAMPLE 7

The reaction of Example 5 was repeated using benzonitrile in place of naphthalene. The conversion of the PFBI was quantitative. The nitrile hydrolyzed during the reaction to give two isomers of perfluorobutylbenzoic acid.

EXAMPLE 8

Example 5 was repeated using toluene in place of the naphthalene. The conversion of the PFBI was quantitative to yield isomers of methyl (perfluorobutyl) benzene.

EXAMPLE 9

Example 5 was repeated using phenol in place of naphthalene. Conversion of the PFBI was quantitative to yield 20% of the expected perfluorobutylphenol and the balance was two unidentified compounds.

EXAMPLE 10

Example 5 was repeated using acetophenone in place of naphthalene. Conversion of the PFBI was quantitative to form all three of the expected isomers.

EXAMPLE 11

Example 5 was repeated using methoxybenzene (anisole) in place of naphthalene. Conversion of PFBI was 96% to yield isomers of methoxy (perfluorobutyl) benzene.

EXAMPLE 12

Example 1 was repeated using PFBI (0.1 mole) and p-chloroaniline (mole) at 170° C. for 12 hours. Conversion of the PFBI was quantitative. The two primary products were 1-chloro-2-(perfluorobutyl)-4-aminobenzene and 4-chloro-2-(perfluorobutyl)-1-aminobenzene.

EXAMPLE 13

Reactor 1 was charged with the following:

|  | g |
|---|---|
| Aniline | 30 |
| PFBI | 40 |
| 50% aqueous potassium carbonate | 40 |

To the above reactants was added 0.1 grams of catalyst consisting of 2% Pd and 0.1% Pt supported on silica microspheres prepared in accordance with Process #1. The contents were heated to 180° C. for hours. After reaction, the contents were emptied, 50 ml water added and the bottom organic layer collected and analyzed by Gas Chromatography-Mass Spectroscopy (GC-MS). There was no unreacted PFBI and the organic layer consisted of three isomers of perfluorobutyl aniline (40% total), 40.6% perfluoropropyl anilino ketone ($NH_2-C_6H_4-CO-C_3F_7$) and 20% of the imine produced from the reaction of this ketone with aniline.

EXAMPLE 14

Reactor I was charged with:

|  | g |
|---|---|
| 25% styrene/maleic acid copolymer average molecular weight 1600 in water | 40 |
| $C_4-C_{10}$ mixed perfluoroalkyl iodides | 30 |
| Solid Potassium hydroxide | 8 |

0.5 grams of the same catalyst as used in Example 1 was added to the contents of the reactor. The contents were heated to 170° C. for 14 hours, cooled, and 100 ml water added and the solution filtered to remove catalyst. The product-containing filtrate was acidified to pH 2 with sulfuric acid to produce a tan precipitate. That precipitate was isolated by centrifugation, slurried with water and centrifuged and then dried. The solids were analyzed by infrared spectroscopy; the incorporation of a perfluoroalkyl group was indicated by two new stretches at 1200 and 700 cm$^1$. The solid was also analyzed for weight percent fluorine and found to contain 25.4% fluorine.

EXAMPLE 15

Reactor I was charged with:

|  | g |
|---|---|
| 1,2-dichlorobenzene | 40 |
| Polystyrene (average molecular weight 45 000) | 10 |
| $C_4-C_{10}$ mixed perfluoroalkyl iodides | 20 |
| 30% aqueous potassium hydroxide | 20 |

To the contents of the reactor was added 0.3 grams of a catalyst consisting of 2% palladium on silica microspheres prepared in accordance with Process #1. The contents were heated and stirred at 200° C. for 12 hours. After reaction, the contents were washed with 50 ml water and the bottom organic layer separated. After filtration to remove catalyst, the organic layer was placed into a flask, heated and stirred to 70° C. at which time, 30 ml methanol was added. The contents were slowly cooled to room temperature and the precipitate filtered and dried to yield 18 of an off-white solid that by elemental analysis contained 25.7% fluorine.

EXAMPLE 16

Reactor I was charged with the following:

|  | g |
|---|---|
| Sodium salt of polystyrene sulfonate (Average molecular weight 70 000) | 20 |
| $C_4$-$C_{10}$ mixed perfluoroalkyl iodides | 40 |
| Solid Potassium hydroxide | 8 |
| Water | 40 |
| Catalyst used in Example 15 | 0.2 |

The contents were heated to 200° C. for 6 hours. After reaction, the contents were filtered to remove catalyst, and 50 ml methanol added to the solution at room temperature. The brown-black precipitate was collected by filtration and dried to give 29 grams of material that by elemental analysis contained 26.4 percent fluorine.

The following two Examples illustrate the effect of employing a phase transfer agent.

EXAMPLE 17

Reactor 1 was charged with the following ingredients:

|  | g |
|---|---|
| Benzene | 20 |
| PFBI | 36 |
| 50% aqueous Potassium carbonate | 40 |
| Catalyst 2% Palladium on carbon | 0.25 |
| Tris-[2-(2-methoxyethoxy)ethyl]amine (phase transfer agent) | 0.05 |

The contents of the reactor were stirred and heated to 170° C. for 3 hours. At the end of this time, a phase cut was taken and the organic phase analyzed by QGC employing an internal standard. Analysis showed there to be a 4.5% yield of perfluorobutyl benzene (PFBB).

EXAMPLE 18

Example 17 was repeated except that the phase transfer agent was omitted. On analysis the yield of PFBB was found to be 2.5%. The above two Examples indicate that the presence of a phase transfer agent further increases the rate of reaction.

EXAMPLE 19

Example 3 was repeated except that the catalyst was 0.1 gram of a 5% palladium on high surface area carbon (surface area 2000 m²/gram) instead of palladium on silica. The yield of perfluorobutyl benzene was 87% with 4% of (III).

EXAMPLE 20

Example 3 was repeated except that the catalyst was 0.1 gram of a 1% cobalt on the same high surface area carbon as in Example 19, instead of palladium on silica. The yield of (I) was 88% with 4% of (III).

I claim:

1. In a process of catalytically polyfluoroalkylating an aromatic compound by reaction of polyfluoroalkyl iodide with the aromatic compound in the presence of a metal catalyst, the improvement comprising (a) carrying out the reaction in the presence of an aqueous inorganic base selected from the group consisting of hydroxides, carbonates and bicarbonates of metals from Group IA and IIA of the Periodic System, (b) in the presence of a metal catalyst selected from the group consisting of rhodium, palladium, platinum, ruthenium, copper, nickel, rhenium and cobalt and mixtures thereof, the amount of water being sufficient to dissolve all of said base under the conditions employed in the said reaction.

2. The process of claim 1 wherein said metal is supported on a high surface area inert carrier.

3. The process of claim 1 or 2 wherein said carrier comprises a high surface area silica, alumina or carbon.

4. The process of claim 3 wherein said carrier comprises porous silica microspheres.

5. The process of claim 3 wherein the mole ratio of aromatic compound to perfluoroalkyl iodide is in the range of about 2:1 to about 4:1.

6. The process of claim 3 wherein the aqueous base comprises a concentrated aqueous solution of an alkali metal hydroxide, carbonate or bicarbonate.

7. The process of claim 6 which is effected at a temperature in the range of about 150° C. to about 250° C. and autogenous pressure.

8. The process of claim 1 wherein said polyfluoroalkyl iodide contains from about 1 to about 20 carbon atoms.

9. The process of claim 8 wherein said polyfluoroalkyl iodide comprises a mixture of perfluoroalkylethyl iodides wherein said alkyl radical contains from about 4 to about 14 carbon atoms.

10. The process of claim 9 wherein catalyst is platinum and/or palladium supported on porous silica.

* * * * *